United States Patent [19]

Minaskanian et al.

[11] Patent Number: 4,879,275
[45] Date of Patent: Nov. 7, 1989

[54] PENETRATION ENHANCERS FOR TRANSDERMAL DELIVERY OF SYSTEMIC AGENT

[75] Inventors: Gevork Minaskanian, Irvine; James V. Peck, Costa Mesa, both of Calif.

[73] Assignee: Nelson Research & Development Co., Irvine, Calif.

[21] Appl. No.: 199,454

[22] Filed: May 27, 1988

Related U.S. Application Data

[63] Continuation-in-part of Ser. No. 103,445, Sep. 30, 1987.

[51] Int. Cl.$^4$ ............... A01N 31/19; A01N 31/40; A01N 43/36
[52] U.S. Cl. ............... 514/24; 514/29; 514/50; 514/179; 514/183; 514/212; 514/269; 514/273; 514/315; 514/316; 514/327; 514/328; 514/330; 514/514; 514/946; 514/947
[58] Field of Search ............... 514/24, 29, 50, 179, 514/183, 212, 269, 273, 315, 316, 327, 328, 330, 514, 946, 947

[56] References Cited

U.S. PATENT DOCUMENTS

| | | | |
|---|---|---|---|
| 3,051,616 | 8/1962 | Drapal | 167/37 |
| 3,085,931 | 4/1963 | Darlington | 167/33 |
| 3,157,641 | 2/1964 | Walles et al. | 260/239.3 |
| 3,306,910 | 2/1967 | Louthan | 260/326.83 |
| 3,306,911 | 2/1967 | Doss | 260/326.83 |
| 3,332,938 | 7/1967 | Mayhew et al. | 260/239.3 |
| 3,341,517 | 9/1967 | Buechel et al. | 260/239 |
| 3,342,673 | 9/1967 | Kaufman et al. | 167/42 |
| 3,391,757 | 6/1975 | Higuchi | 424/310 |
| 3,551,544 | 12/1970 | Herschler | 424/7 |
| 3,598,122 | 8/1971 | Zaffaroni | 128/268 |
| 3,598,123 | 8/1971 | Zaffaroni | 128/268 |
| 3,678,156 | 7/1972 | Mac Millan et al. | 424/68 |
| 3,731,683 | 5/1973 | Zaffaroni | 128/268 |
| 3,742,951 | 5/1973 | Zaffaroni | 128/268 |
| 3,814,097 | 6/1974 | Ganderton et al. | 128/268 |
| 3,823,152 | 7/1974 | Morimoto et al. | 260/293.69 |
| 3,865,814 | 2/1975 | Lussi et al. | 260/239.3 |
| 3,921,636 | 11/1975 | Zaffaroni | 128/260 |
| 3,954,966 | 5/1976 | Lim et al. | 424/81 |
| 3,960,922 | 6/1976 | Baker et al. | 260/465 |
| 3,966,806 | 6/1976 | Baker et al. | 260/558 |
| 3,972,995 | 8/1976 | Tsuk et al. | 424/28 |
| 3,989,815 | 11/1976 | Rajadhyaksha | 424/60 |
| 3,989,816 | 11/1976 | Rajadhyaksha | 424/60 |
| 3,991,203 | 11/1976 | Rajadhyaksha | 424/274 |
| 3,993,072 | 11/1976 | Zaffaroni | 128/260 |
| 3,993,073 | 11/1976 | Zaffaroni | 128/260 |
| 3,996,934 | 12/1976 | Zaffaroni | 128/268 |
| 4,021,224 | 5/1977 | Pallos et al. | 71/88 |
| 4,031,894 | 6/1977 | Urfahart | 128/268 |
| 4,060,084 | 11/1977 | Chandrasek et al. | 128/260 |
| 4,069,307 | 1/1978 | Higuchi et al. | 128/260 |
| 4,077,407 | 3/1978 | Theemes | 128/260 |
| 4,118,500 | 10/1978 | Pritzlaff et al. | 424/267 |
| 4,122,170 | 10/1978 | Rajadhyaksha | 424/180 |
| 4,201,211 | 5/1980 | Chandrasek et al. | 128/268 |
| 4,230,105 | 8/1981 | Hussain et al. | 424/156 |
| 4,264,594 | 4/1981 | McGovern et al. | 424/244 |
| 4,284,648 | 8/1981 | Hussain et al. | 424/330 |
| 4,292,299 | 9/1981 | Suziki | 128/156 |
| 4,292,303 | 9/1981 | Keith et al. | 128/265 |
| 4,310,525 | 1/1982 | Nelson | 424/244 |
| 4,311,481 | 1/1982 | Nelson | 8/561 |
| 4,316,893 | 2/1982 | Rajadhyaksha | 424/180 |
| 4,364,952 | 12/1982 | Materne | 424/266 |
| 4,405,616 | 9/1983 | Rajadhyaksha | 424/244 |
| 4,415,563 | 11/1983 | Rajadhyaksha | 424/244 |
| 4,423,040 | 12/1983 | Rajadhyaksha | 424/180 |
| 4,424,210 | 1/1984 | Rajadhyaksha | 424/180 |
| 4,440,777 | 4/1984 | Zupan | 424/274 |
| 4,444,762 | 4/1984 | Rajadhyaksha | 424/180 |
| 4,525,199 | 6/1985 | Rajadhyaksha | 514/788 |
| 4,537,776 | 8/1985 | Cooper | 514/424 |
| 4,552,872 | 11/1985 | Cooper | 424/175 |
| 4,557,934 | 12/1985 | Cooper | 424/128 |
| 4,562,075 | 12/1985 | Rajadhyaksha | 514/788 |
| 4,565,823 | 1/1986 | Ohata et al. | 514/356 |
| 4,605,670 | 8/1986 | Saito | 514/619 |
| 4,620,949 | 11/1986 | Lin | 540/525 |
| 4,621,143 | 11/1986 | McGovern et al. | 546/245 |
| 4,626,539 | 12/1986 | Aungst et al. | 514/282 |

FOREIGN PATENT DOCUMENTS

| | | |
|---|---|---|
| 947764 | 5/1974 | Canada . |
| 0104037 | 3/1984 | |
| 0129284 | 12/1984 | |
| 0164998 | 12/1985 | |
| 1102521 | 2/1968 | United Kingdom . |
| 1421743 | 1/1976 | United Kingdom . |
| 1421744 | 1/1976 | United Kingdom . |
| 2078725 | 1/1982 | United Kingdom . |

OTHER PUBLICATIONS

Bennett, S. L. et al., "Optimization of Bioavailability of Topical Steroids: Non-Occluded Penetration Enhanc- (List continued on next page.)

Primary Examiner—Curtis R. Davis
Attorney, Agent, or Firm—Robert J. Baran; June M. Bostich

[57] ABSTRACT

This invention relates to a method for administering systemically active agents including therapeutic agents through the skin or mucosal membranes of humans and animals in a transdermal device or formulation comprising topically administering with said systemic agent an effective amount of a membrane penetration enhancer having the structural formula

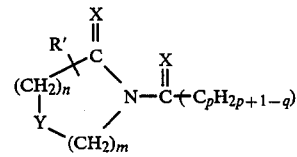

wherein X represents sulfur, oxygen or 2 hydrogen radicals; Y represents $-CH_2-$, $-NH-$ or oxygen; n and m are integers of from 1 to 3; p is an integer of from 3 to 17; wherein $p \geq 9$; q is 2, 4, 6 or 8; and R' is selected from the group consisting of H, a lower alkyl group having from 1 to 4 carbon atoms, phenyl, lower alkyl or halogen substituted phenyl, acetamido, halogen, piperidinyl, lower alkyl or halogen substituted piperidinyl, carbalkoxy, carboxamide, and alkanoyl.

13 Claims, No Drawings

OTHER PUBLICATIONS ers Under Thermodynamic Control", *J. Pharm. Pharmacol.*, 37(5): 298–304, 1985.

Goldman, L. et al., "Preliminary Investigative Studies with DDT in Dermatologic and Plastic Surgery", *Lasers Surg Med*, 5(5): 453–456, 1985.

Chow, DS-L et al., "Concentration-Dependent Enchancement of 1-Dodecylazacycloheptan-2-one on the Percutaneous Penetration Kinetics of Triamcinolone Acetonide", *J. Pharm Sci*, 73(12):1794–1799, 1984.

DeClercg, E., "Topical Treatment of Cutaneous Herpes Simplex Virus Infection in Hairless Mice with (E)-- 5-(2-Bromovinyl)-2'-Dioxyurdine and Related Compounds", *Antimicrob Agents Chemother*, 26(2): 155–159, 1984.

Goodman, M. et al., Differential Scanning Colorimetry (DSC) of Human Stratum Corneum: Effect of Azone, Presentation at the British Pharmaceutical Conference Leeds, 1985.

Hadgraft, J. et al., "Facilitated Transport of Sodium Salicylate Across an Artificial Lipid Membrane by Azone", *J. Pharm Pharmacol*, 37(10): 725–727, 1985.

Higuchi, W. I., "Macro- and Micro-Physical Chemical Considerations in Understanding Drug Transport in the Stratum Corneum", Second Int'l Symp. Recent Advances in Drug Delivery Systems, Salt Lake City, Utah, 1985.

Higuchi, W. I. et al., "Tropical Delivery of Antiviral Agents: In Vivo/In Vitro Correlations", Proc. Int. Symp., pp. 1–7, 1984.

Hoelgaard, A., "Dermal Drug Delivery-Improvement by Choice of Vehicle or Drug Derivative", 2nd Int'l. Symp Recent Adv Drug Delivery Systems, 1985.

Chemical Abstracts: 69:86313p, 82:39533u, 83:93905e, 83:1758d, 83:91780g, 102:183860x, 104:174644u.

Liang, W. Q. et al., "Affect of Axone of Local Pharmacokinetics of Para-Aminobenzoic Acid in Skin", 11th Int'l Symp., Controlled Release Bioactive Mat., 1984.

Maibach, H. I. et al., "Phototoxicity (Photoirritation) of Topical and Systemic Agents", *Advances in Modern Toxicology*, 4:211–223.

Marzulli F. N. et al., "Contact Allergy: Predictive Testing in Humans, Advances", in *Modern Toxicology*, 4:253–372, 1977.

McCullogh, J. L. et al., "Regulation of Epidermal Prolifieration in Mouse Epidermis by Combination of Difluoromethyl Ornithine (DFMO) and Methylglyoxal Bis (guancylhydrazone) (MGBG)", *J. Invest. Dermatol*, 85(6): 518–521, 1985.

McCullogh, J. L. et al., "Development of a Topical Hematoporphysin Derivative Formulation: Characterization of Photosensitizing Effects. In Vivo", *J. Invest Dermatol*, 81(6): 528–532, 1983.

Ohshima, T. et al., "Enhancing Effect of Absorption Promoters on Percutaneous Absorption of a Model Dye (6-Carboxyfluorescein) as Poorly Absorbable Drugs. II, Study on the Absorption Promoting Effect of Azone", *J. Pharm Dyn* 8:900–905, 1985.

Ryatt, J. K., "Pharmacodynamic Measurement of Percutaneous Penetration Enhancement in Vivo", *J. Pharm Sci* 75:(4) 374–377, 1986.

Stoughton, R. B., "Azone as a Promoter of Percutaneous Absorption", (1983), *Acta Pharm* 20(1):62.

Shannon, W. M. et al., "Influence of 1-Dodecylazacydoheptan-2-one (Azone) on the Topical Therapy of Cutaneous Herpes Simples Virus Type 1 Infection in Hairless Mice with 2', 3'-D-arabinofuranosyladenine", *J. Pharm Sci* 74(11):1157–1161, 1985.

Spruance, S. I. et al., "Effect of Azone and Propylene Glycol on Penetration of Trifluorothymidine Through Skin and Efficacy of Different Topical Formulations Against Cutaneous Herpes Simplex Virus Infections in Guinea Pigs", *Antimicrob Agent Chemother* 25(5):819–823, 1984.

Stoughton, R. B. et al., "Azone ®: A New Non-Toxic Enhancer of Cutaneous Penetration", *Drug Dev. Ind. Pharm* 9(4):725–744, 1983.

Stoughton, R. B., "Azone Enhances Percutaneous Penetration", IN: Psoriasi Proceedings of the Third Int'l Sump., 397–398, 1982.

Stoughton, R. B., "Enhanced Percutaneous Penetration with 1-Dodecylazacycloheptan-2-one", *Archives of Derm* 118:474–477, 1982.

Sugibayashi, K. et al., "Effect of the Absorption Enhancer, Azone, on the Transport of 4-Fluorouracil Across Hairless Rat Skin", *J. Pharm Pharm* 37(8):578–580, 1985.

Toutitou, E. et al., "Effect of Propylene Glycol, Azone and N-Decylmethyl Suphoxide on Skin Permeation Kinetics of 5-Fluorouracil", *Int J. Pharm* 1(27): 89–98, 1985.

Wooton, P. K. et al., "Vehicle Effect on Topical Drug Delivery, III, Effect of Azone on the Cutaneous Permeation of Metronidazole and Propylene Glycol", *Int J Pharm* 1(24):19–26, 1985.

Rajadhyaksha, V. et al., "Transdermal Delivery of ISDN from Hercon Patches Containing Azone", Proceed Intern Symp Control Rel Biact Mater, 12, (222-323), 1985.

Zoler, M. L., "Skin Penetration of Antiherpes Drugs Can Be Enchanced by Azone", Dermatology Times, 5(2), 1984.

Hadgraft, J., "Percutaneous Absorption", Cos & Toiletries 100, 32–28, 19.

Mehr, A. Z., "Evaluation of Commercial and Experimental Repellents Against Xenopsylla Cheopis (Siphonaptera: Pulicidae)", *J. Med Entomol*, vol. 21, No. 6: 665–669.

Skinner, W. A. et al., "Tick Repellents II: N-Substituted Azacyclopentanones and Azacyclopentenones", J. Pharm Sci, 72(11):1354, 1983.

Vaidyanathan, R. et al., "Dodecylazacycloneptan-2-- one (Azone ®) Enhanced Delivery of Drugs into the Epidermis I: Effect of Enhancer Concentration on the Permeability of Select Compounds", Abstract No. 97, *Pharm Sci* 12(2): 126, 1982.

Vaidyanathan, R. et al., "Dodecylazacycloheptan-2-- One (Azone ®) Enhanced II: Permeation of Ara-A-5-'-Valerate through Hairless Mouse Skin from Prototype Formulations", Abstract No. 98, *Pharm Sci* 12(2): 126, 1982.

PENETRATION ENHANCERS FOR TRANSDERMAL DELIVERY OF SYSTEMIC AGENT

REFERENCE TO EARLIER FILED APPLICATIONS

This application is continuation-in-part of U.S. Ser. No. 103,445, entitled COMPOSITIONS COMPRISING 1-OXO-OR THIOHYDROCARBYL SUBSTITUTED AZACYCLOALKANES, filed on Sept. 30, 1987.

BACKGROUND OF THE INVENTION (1.) Field of the Invention

The invention generally relates to an improved method of drug delivery. More particularly, the invention relates to an improved membrane penetration enhancer for use in the transdermal delivery of systemically active drugs to humans and animals.

(2.) Background of the Prior Art

For some years, pharmaceutical researchers have sought an effective means of introducing drugs into the bloodstream by applying them to unbroken skin. Among other advantages, such administration can provide a comfortable, convenient, and safe way of giving many drugs now taken orally or infused into veins or injected intramuscularly.

Using skin as the portal for drug entry offers unique potential, because transdermal delivery permits close control over drug adsorption. For example, it avoids factors that can cause unpredictable absorption from the gastrointestinal tract, including: changes in acidity, motility, and food content. It also avoids initial metabolism of the drug by the liver. Thus, controlled drug entry through skin can achieve a high degree of control over blood concentrations of drug.

Close control over drug concentrations in blood can translate readily into safer and more comfortable treatment. When a drug's adverse effects occur at higher concentrations than its beneficial ones, rate control can maintain the concentrations that evoke only—or principally—the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and that reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over a prolonged period of time to obtain a uniform delivery rate and blood level of drug. Commencement and termination of drug therapy are initiated by the application and removal of the dosing devices from the skin. Uncertainties of administration through the gastrointestinal tract and the inconveniences of administration by injection are eliminated. Since a high concentration of drug never enters the body, problems of pulse entry are overcome and metabolic half-life is not a factor of controlling importance.

U.S. Pat. Nos. 3,989,815; 3,989,816; 3,991,203; 4,122,170; 4,316,893; 4,415,563; 4,423,040; 4,424,210; and 4,444,762 generally describe a method for enhancing the topical (as contrasted to the systemic) administration of physiologically active agents by combining such an agent with an effective amount of a penetration enhancer and applying the combination topically to humans or animals, in the form of creams, lotions, gels, etc.

Penetration enhancers for enhancing systemic administration of therapeutic agents transdermally are cited in U.S. Pat. Nos. 4,405,616; 4,462,075; 4,031,894, 3,996,934; and 3,921,636.

SUMMARY OF THE INVENTION

It has been discovered that the penetration enhancers previously disclosed in U.S. patent application Ser. No. 103,445 filed on Sept. 30, 1987, to enhance topical delivery of physiologically active agents also enhance the transdermal delivery of systemically active agents through the skin or other body membranes of humans and animals directly into the bloodstream.

The invention therefore provides a method for topically administering systemically active agents through the skin or mucosal membranes of humans and animals, utilizing a transdermal device or formulation, wherein the improvement in said method comprises topically administering with said systemic agent an effective amount of a membrane penetration enhancer having the general structural formula:

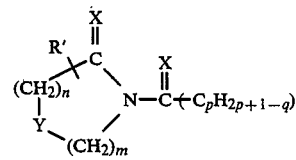

wherein X may represent oxygen, sulfur or 2 hydrogen radicals; Y may represent —CH$_2$—, —NH— or oxygen; n and m are integers of from 1 to 3; p is an integer of from 3 to 17; q is 2, 4, 6 or 8; wherein p is $\geq 9$; and R' is selected from the group consisting of H, a lower alkyl group having from 1 to 4 carbon atoms, phenyl, lower alkyl or halogen substituted phenyl, acetamido, halogen, piperidinyl, carbalkoxy, carboxamide, and alkanoyl; Preferably, R' is H, at least the X on the side chain is oxygen and the X on the ring is oxygen or 2 hydrogen radicals and q is 2. In a more preferred embodiment of the present invention, p is 4–16, e.g. 10.

The invention also provides an improved method for administering systemically active therapeutic agents topically through the skin of humans in a transdermal device or formulation to obtain therapeutic blood levels of the therapeutic agent, wherein the improvement in said method comprises the use of an effective skin penetration enhancing amount of the above membrane penetration enhancer, with said therapeutic agent.

DETAILED DESCRIPTION OF THE INVENTION

The unsaturated 1-oxohydrocarbyl-substituted derivatives of azacycloalkanes, useful in the method of the present invention include compounds represented by the general formula:

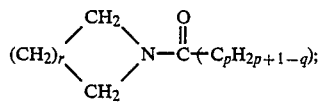  I

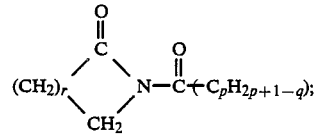  II and

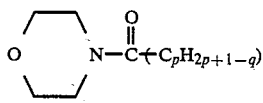  III wherein r is an integer of from 2–6 and p and q are defined above.

Many of these 1-oxohydrocarbyl-substituted derivatives, useful as penetration-enhancing additives in the compositions of the instant invention, are well known. They may be made by the methods described in U.S. patent application 103,445, filed on Sept. 30, 1987. Typical examples of compounds represented by the above general formula that effect systemic penetration include:

N-(1-oxododec-10-enyl)morpholine
2',6'-dimethyl-N-(1-oxohexadec-10-enyl)morpholine
2',6'-dimethyl-N-(1-oxooctadec-10-enyl)morpholine
2',6'-dimethyl-N-(1-oxododec-10-enyl)morpholine
2',6'-dimethyl-N-(1-oxotridec-11-enyl)morpholine
2',6'-dimethyl-N-(1-oxotetradec-12-enyl)morpholine
2',6'-dimethyl-N-(1-oxoundec-10-enyl)morpholine
N-(1-oxooctadec-17-enyl)morpholine
N-(1-oxonon-8-enyl)morpholine
N-(1-oxodec-9-enyl)morpholine
N-(1-oxododec-10-enyl)morpholine
N-(1-oxohexadec-15-enyl)morpholine
N-(1-oxotetradec-13-enyl)morpholine
N-(1-oxooct-7-enyl)morpholine
N-(1-oxohex-5-enyl)morpholine
N-(1-oxohept-6-enyl)morpholine
N-(1-oxoopent-4-enyl)morpholine
N-(1-oxoundec-2-enyl)morpholine
N-(1-oxodeca-2,3-dienyl)morpholine
N-(1-oxononadec-18-enyl)morpholine
N-(1-oxoundec-10-enyl)morpholine
N-(1-oxoheptadec-15-enyl)morpholine
N-(1-oxopentadec-14-enyl)morpholine
2,6-dimethyl-4-(1-oxodec-17-enyl)morpholine
N-(1-oxotridec-12-enyl)morpholine
N-(1-oxododec-10-enyl)azacycloheptane
2,6-dimethyl-N-(1-oxohexadec-10-enyl) azacycloheptane
2,6-dimethyl-N-(1-oxooctadec-10-enyl)azacycloheptane
2,6-dimethyl-N-(1-oxododec-10-enyl)azacycloheptane
2,6-dimethyl-N-(1-oxotridec-11-enyl)azacycloheptane
2,6-dimethyl-N-(1-oxotetradec-12-enyl)azacycloheptane
2,6-dimethyl-N-(1-oxoundec-10-enyl)azacycloheptane
N-(1-oxooctadec-17-enyl)azacycloheptane
N-(1-oxonon-8-enyl)azacycloheptane
N-(1-oxodec-9-enyl)azacycloheptane
N-(1-oxododec-10-enyl)azacycloheptane
N-(1-oxohexadec-15-enyl)azacycloheptane
N-(1-oxotetradec-13-enyl)azacycloheptane
N-(1-oxopentadec-14-enyl)azacyclohept-2-one
2,6-dimethyl-N-(1-oxodec-17-enyl)azacyclohept-2-one
N-(1-oxotridec-12-enyl)azacyclohept-2-one Typical systemically active agents which may be delivered transdermally are therapeutic agents which are sufficiently potent that they can be delivered through the skin or other membrane to the bloodstream in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparions including calcium channel blockers, betablockers, antiarrhythmics, antihypertensives, diuretics, vasodialators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

Dosage forms for application to the skin or other membranes of humans and animals include creams, lotions, gels, ointments, suppositories, sprays, aerosols, buccal and sub-lingual tablets and any one of a variety of transdermal devices for use in the continuous administration of systemically active drugs by absorption through the skin, oral mucosa or other membranes, see, for example, one or more of U.S. Pat. Nos. 3,598,122; 3,598,123; 3,731,683; 3,742,951; 3,814,097; 3,921,636; 3,972,995; 3,993,072; 3,993,073; 3,996,934; 4,031,894; 4,060,084; 4,069,307; 4,201,211; 4,230,105; 4,292,299 and 4,292,303. U.S. Pat. No. 4,077,407 and the foregoing patents also disclose a variety of specific systemically active agents which may also be useful in transdermal delivery, which disclosures are hereby incorporated herein by this reference.

Typical inert carriers which may be included in the foregoing dosage forms include conventional formulating materials, such as, for example, water, isopropyl alcohol, gaseous fluorocarbons, ethyl alcohol, polyvinyl pyrrolidone, propylene glycol, fragrances, gel-producing materials such as "Carbopol", stearyl alcohol, stearic acid, spermaceti, sorbitan monooleate, "Polysorbates", "Tweens", sorbital, methylcellulose, etc.

Systemically active agents are used in amounts calculated to achieve and maintain therapeutic blood levels in a human or animal over the period of time desired. These amounts vary with the potency of each systemically active substance, the amount required for the desired therapeutic or other effect, the rate of elimination or breakdown of the substance by the body once it has entered the bloodstream and the amount of penetration-enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The amount of penetration enhancer which may be used in the invention varies from about 1 to 100 percent although adequate enhancement of penetration is generally found to occur in the range of about 1 to 100 percent although adequate enhancement of penetration is generally found to occur in the range of about 1 to about 10 percent by weight of the formulation to be delivered. The penetration-enhancer disclosed herein may be used in combination with the active agent or may be used separately as a pre-treatment of the skin or other body membrane though which the systemically-active agent is intended to be delivered.

The invention is further illustrated by the following examples which are illustrative of a specific mode of practicing the invention and is not intended as limiting the scope of the appended claims.

EXAMPLE 1

A composition, in the form of a gel, suitable for transdermal delivery of haloperidol, an antidyskinetic or antipsychotic drug, is prepared by mixing the following components in the given concentration.

| Component | Weight % |
|---|---|
| Haloperidol | 1-5 |
| N—(1-Oxoundec-10-enyl) azacycloheptan-2-one | 1-10 |
| Carbopol 934 P (Available from B. F. Goodrich) | 0.5-2 |
| Neutralizing Agent (NaOH) | q.s. |
| Tween-20 (Available from Atlas Chemical, a Div. of I.C.I.) | 1-10 |
| Preservative (Sorbic Acid) | q.s. |
| Antioxidant (Ascorbic Acid) | q.s. |
| Chelating Agent (Disodium salt of ethylenediaminetetraacetic acid) | q.s. |
| Deionized Water | q.s. to 100 |

This composition is topically applied to the skin of a human subject and after the passage of a suitable period of time haloperidol is found in the bloodstream of said subject.

EXAMPLE 2

When an amine, e.g., triethylamine or triethanolamine, is substituted for NaOH the results are substantially similar, i.e., a topical composition suitable for transdermally delivering haloperidol to the bloodstream is obtained.

EXAMPLE 3

When potassium sorbate, or a lower alkyl paraben, e.g., methyl, ethyl, propyl, or butyl paraben are substituted for the preservative of the composition of Example 1, the results are substantially similar, i.e., a topical composition suitable for the transdermal delivery of haloperidol to the bloodstream is obtained.

EXAMPLE 4

When ascorbyl palmitate, Vitamin E, thioglycerol, thioglycolic acid, sodium formaldehyde sulfoxylate, BHA, BHT, propyl gallate or sodium metabisulfite are substituted for the antioxidant of the composition formulated in Example 1, the results are substantially similar in that a topical composition suitable for transdermally delivering haloperidol to the bloodstream is obtained.

EXAMPLE 5

The composition of Example 1 is prepared in the form of a sodium alginate gel by mixing the following components in the following given concentrations:

| Component | Weight % |
|---|---|
| Haloperidol | 1-5 |
| N—(1-oxoundec-10-enyl) azacycloheptan-2-one | 1-10 |
| Sodium Alginate | 0.5-5 |
| Calcium Salts | q.s. |
| Tween-20 | 1-10 |
| Preservative* | q.s. |
| Antioxidant** | q.s. |
| Chelating Agent*** | q.s. |
| Deionized Water | to 100 |

*Suitable preservatives are those used in Example 3 as well as sorbic acid.
**Suitable antioxidants are those used in Example 4 including ascorbic acid.
***The chelating agent is the disodium salt of ethylenediaminetetraacetic acid.

This composition when applied topically is found to transdermally deliver haloperidol to the bloodstream of a subject.

EXAMPLE 6

The composition of Example 1 is prepared in the form of a hydrophilic cream by mixing the following components.

| Component | Weight % |
|---|---|
| Oil Phase | |
| Cetyl Alcohol | 5-15 |
| Stearyl Alcohol | 1-5 |
| N—(1-oxoundec-10-enyl) azacycloheptan-2-one | 0.5-10 |
| Glycerol Monostearate | 2-7 |
| Water Phase | |
| Sodium Laurylsulfate | 0.1 |
| Solvent* | 2-20 |
| Tween-20 | 1-5 |
| Water | q.s. to 100 |

*Suitable solvents are propylene glycol, glycerin, alcohols, for example, ethyl alcohol, isopropyl alcohol, etc., and polyethylene glycols.

The oil phase and the water phase is made up separately, and then agitated to form an emulsion. (When, as in Example 8, the active ingredient, is other than haloperidol, depending on its lipophilicity, it will be distributed in the oil or water phase.) This hydrophilic cream, when applied topically to the skin of a human, is found to transdermally deliver haloperidol into the bloodstream.

EXAMPLE 7

The composition of the instant invention may also be delivered by use of a polymeric matrix. For example, a solid polymer such as cellulose triacetate, polyvinyl acetate, terpolymers and copolymers of polyvinyl alcohol and polyvinyl acetate, and silicon elastomers is imbibed with a liquid having the following components in the given concentrations.

| Component | Weight % |
| --- | --- |
| Polymer | 5-40 |
| Haloperidol | q.s. |
| N—(1-oxoundec-10-enyl) azacycloheptane-2-one | 0.5-80 |
| Solvent* | 5-90 |
| Surfactant** | 1-10 |
| Preservative*** | q.s. |
| Antioxidant**** | q.s. |

*Solvents may be the solvents used in Example 6 above.
**The Surfactant may be Tween-20, glycerol monostearate or sodium laurylsulfate, etc.
***The preservative may be any of the preservatives used in Example 3 above.
****The antioxidants may be any of those used in Example 4 above.

When solid matrix, containing the active ingredients formulated above, is contacted with the skin of a human subject, after a period of time the active agent is found in the bloodstream of said subject.

EXAMPLE 8

Examples 1 to 7 are repeated except that the following active ingredients in the given concentrations are substituted for haloperidol:

| Active Ingredient | Weight % |
| --- | --- |
| Isosorbide Dinitrate | 5-15 |
| Nitroglycerin | 1-5 |
| Estradiol | 1-5 |
| Clonidine | 0.5-3 |
| Propranolol | 1-5 |
| Indomethacine | 5-15 |
| Nifedipine | 1-5 |
| Nicardipine | 1-5 |
| Diclorofenac | 5-15 |
| Metaproterenol | 1-5 |

Similar results are obtained in that the active ingredient is transdermally delivered to the bloodstream of an animal.

EXAMPLE 9

Examples 1 to 8 are repeated except that the compounds exemplified on page 7 (except for N-(1-oxoundec-10-enyl) azacycloheptan-2-one are substituted for N-(1- oxoundec-10-enyl)azacycloheptan-2-one. Similar results are obtained in that the active ingredients are transdermally delivered to the bloodstream of an animal.

N-(1-oxoundec-10-enyl)azacycloheptane and N-(1-oxoundec-10-enyl)morpholine are specially suitable for substituted for N-1-oxoundec-10-enyl)azacycloheptane-2-one in Examples 1 to 8.

While particular embodiments of the invention have been described it will be understood of course that the invention is not limited thereto since many obvious modifications can be made and it is intended to include within this invention any such modifications as will fall within the scope of the appended claims.

Having now described the invention, we claim:

1. A method for topically enhancing penetration of systemically active agents through the skin or mucosal membranes of humans and animals and into the bloodstream, wherein said method comprises the topical administration of an effective amount of a systemically active agent and an effective systemic penetrating amount of a membrane penetration enhancer having the structural formula $$\begin{array}{c} X \\ R' \; \| \\ \diagdown C \\ (CH_2)_n \diagup \quad \diagdown \quad \overset{X}{\|} \\ | \qquad \qquad N-C-(C_pH_{2p+1-q}) \\ Y \diagdown \qquad \diagup \\ (CH_2)_m \end{array}$$

wherein X represents sulfur, oxygen or 2 hydrogen radicals; Y represents —CH$_2$—, —NH— or oxygen; n and m are integers of from 1 to 3; p is an integer of from 3 to 17; wherein p≧9; q is 2, 4, 6 or 8; and R' is selected from the group consisting of H, a lower alkyl group having from 1 to 4 carbon atoms, phenyl, lower alkyl or halogen substituted phenyl, acetamido, halogen, piperidinyl, lower alkyl or halogen substituted piperidinyl, carbalkoxy, carboxamide, and alkanoyl.

2. The method in claim 1 wherein p is between 4 and 16.

3. The method of claim 2 wherein p is 10.

4. The method of claim 1 wherein the systemically active agent is a therapeutic agent.

5. The method of claim 4 wherein the administration is concurrent.

6. The method of claim 1 wherein the membrane penetration enhancer is selected from the group consisting of N-(1-oxoundec-10-enyl)azacycloheptane-2-one, N-(1-oxoundec-10-enyl)azacycloheptane and N-(1-oxoundec-10-enyl)morpholine.

7. The method of claim 1 wherein the systemically active agent is selected from the group consisting of haloperidol, isosorbide dinitrate, nitrogycerin, estradiol, clonidine, propranolol, indomethacin, nifedipine, nicardipine, diclorofenac and metaproterenol.

8. The method of claim 8 wherein the systemically active agent is selected from the group consisting of haloperidol, isosorbide dinitrate, nitroglycerin, estradiol, clonidine, propranolol, indomethacin, nifedipine, nicardipine, diclorofenac and metaproterenol.

9. A method for topically administering an effective amount of a systemic physiologically active agent to a human or animal comprising administering to a human or animal an effective amount of a physiologically active systemic agent and a non-toxic systemically penetrating amount of penetration-enhancing agent represented by the general formula $$\begin{array}{c} CH_2 \qquad O \\ \diagup \diagdown \quad \| \\ (CH_2)_r \qquad N-C-(C_pH_{2p+1-q}); \\ \diagdown \diagup \\ CH_2 \end{array} \qquad \text{I}$$

-continued

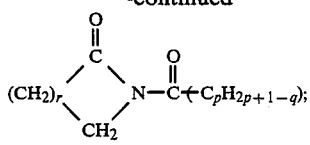
II and

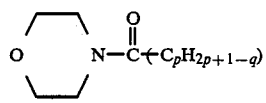
III wherein r is an integer of from 2-6, p is an integer of from 3 to 17 and q is 2.

10. The method of claim 9 wherein the systemically active agent is selected from the group consisting of N-(1-oxoundec-10-enyl)azacycloheptane-2-one, N-(1-oxoundec-10-enyl)azacycloheptane and N-(1-oxoundec-10-enyl)morpholine.

11. The method of claim 9 wherein the systemically active agent is a therapeutic agent.

12. The method of claim 10 wherein the systemically active agent is selected from the group consisting of haloperidol, isosorbide dinitrate, nitroglycerin, estradiol, clonidine, propranolol, indomethacin, nifedipine, nicardipine, diclorofenac and metaproterenol.

13. The method of claim 9 wherein the systemically active agent is selected from the group consisting of haloperidol, isosorbide dinitrate, nitroglycerin, estradiol, clonidine, propranolol, indomethacin, nifedipine, nicardipine, diclorofenac and metaproterenol.

* * * * *